US011084307B2

(12) United States Patent
Horn et al.

(10) Patent No.: US 11,084,307 B2
(45) Date of Patent: Aug. 10, 2021

(54) HEAT-SENSITIVE RECORDING MATERIAL

(71) Applicant: PAPIERFABRIK AUGUST KOEHLER SE, Oberkirch (DE)

(72) Inventors: Michael Horn, Offenburg (DE); Timo Stalling, Appenweier (DE); Kerstin Zieringer, Achern (DE)

(73) Assignee: PAPIERFABRIK AUGUST KOEHLER SE, Oberkirch (DE)

( * ) Notice: Subject to any disclaimer, the term of this patent is extended or adjusted under 35 U.S.C. 154(b) by 229 days.

(21) Appl. No.: 16/485,110

(22) PCT Filed: Jan. 18, 2018

(86) PCT No.: PCT/EP2018/051208
§ 371 (c)(1),
(2) Date: Aug. 9, 2019

(87) PCT Pub. No.: WO2018/145874
PCT Pub. Date: Aug. 16, 2018

(65) Prior Publication Data
US 2020/0070556 A1 Mar. 5, 2020

(30) Foreign Application Priority Data
Feb. 10, 2017 (DE) .......................... 102017102702.5

(51) Int. Cl.
*B41M 5/333* (2006.01)
*B41M 5/327* (2006.01)
*C07C 311/47* (2006.01)
*C07C 311/21* (2006.01)

(52) U.S. Cl.
CPC ........ *B41M 5/3333* (2013.01); *B41M 5/3275* (2013.01); *C07C 311/21* (2013.01); *C07C 311/47* (2013.01); *C07C 2601/16* (2017.05)

(58) Field of Classification Search
None
See application file for complete search history.

(56) References Cited

U.S. PATENT DOCUMENTS 5,665,675 A * 9/1997 Nagai .................. B41M 5/3333
503/209
2015/0284321 A1* 10/2015 Sakai .................. B41M 5/3336
428/195.1

FOREIGN PATENT DOCUMENTS

| EP | 71839 A1 | 2/1983 |
| EP | 0526072 A1 | 2/1993 |
| EP | 0620122 A1 | 10/1994 |
| EP | 0633145 A1 | 1/1995 |
| EP | 0693386 A1 | 1/1996 |
| EP | 2923851 A1 | 9/2015 |
| JP | 6227142 A | 8/1994 |
| JP | 3509082 A | 1/1996 |
| JP | 8197851 A | 8/1996 |
| JP | 8244355 A | 9/1996 |
| JP | 10230681 A | 9/1998 |
| JP | 11268422 A | 10/1999 |
| WO | 2000035679 A1 | 6/2000 |

OTHER PUBLICATIONS

International Search Report for PCT Application No. PCT/EP2018/051208, dated May 9, 2018, 4 pages.

* cited by examiner

*Primary Examiner* — Amy C Bonaparte
(74) *Attorney, Agent, or Firm* — Fay Sharpe LLP

(57) ABSTRACT

The invention relates to a compound of the formula (I) Ar(NHSO$_2$Ar$^1$)l(SO$_2$NHAr$^1$)$_m$(NHC(O)NHAr$^2$)$_n$ (I), wherein l and m independently of one another are 0, 1, 2, 3, and/or 4 and the sum of l+m is equal to or more than 1, n is 2, 3, 4, or 5, Ar is a benzol group which is substituted (l+m+n) times, Ar$^1$ is an unsubstituted or substituted aromatic group, and Ar$^2$ is an unsubstituted or substituted phenyl group or a benzoyl group. The invention also relates to a heat-sensitive recording material comprising a carrier substrate and a heat-sensitive color-forming layer which contains at least one color former and at least said color developer.

20 Claims, No Drawings

HEAT-SENSITIVE RECORDING MATERIAL

The invention relates to a colour developer, a heat-sensitive recording material comprising a carrier substrate, and heat-sensitive colour-forming layer containing at least this colour developer, and the use of the phenol-free colour developer contained in the heat-sensitive recording material.

Heat-sensitive recording materials for use in direct thermal printing which have a heat-sensitive colour-forming layer (thermal reaction layer) applied to a carrier substrate have long been known. A colour former and a colour developer are usually present in the heat-sensitive colour-forming layer and react with one another under the action of heat and thus lead to a development of colour. Inexpensive phenolic colour developers are widespread, for example bisphenol A and bisphenol S, with which it is possible to obtain heat-sensitive recording materials which have an acceptable performance profile for numerous applications. Also known are heat-sensitive recording materials which contain a non-phenolic colour developer in the heat-sensitive colour-forming layer. These materials were developed in order to improve the resistance of the printed text, especially also when the printed heat-sensitive recording material is stored over a longer time or comes into contact with hydrophobic substances, such as plasticiser-containing materials or oils. Especially against the background of public discussions regarding the toxic potential of bisphenolic chemicals, the interest in non-phenolic colour developers has increased greatly. In this regard the objective has been to avoid the disadvantages of the bisphenolic colour developers, however the technical performance properties that can be attained with phenolic colour developers should at least be maintained, and preferably enhanced.

The comprehensive prior art with regard to non-phenolic colour developers makes it possible to identify common structural features in spite of the wide chemical diversity of these materials.

A 1,3-disubstituted (thio)ureido substructure (Y—NH—C(X)—NH—Z where X=S, O) is a common feature of numerous non-phenolic colour developers. By appropriate selection of the groups Y and Z it is possible to modulate the functional properties relevant for suitability as a colour developer.

Colour developers with sulfonyl-urea structures (—SO$_2$—NH—CO—NH—) are widespread as colour developers since they can be produced relatively easily and the heat-sensitive recording materials produced with their use have relatively good application properties.

EP 0 526 072 A1 and EP 0 620 122 D1 disclose colour developers from the class of aromatic sulfonyl-(thio)ureas. They can be used to produce heat-sensitive recording materials that are characterised by a relatively high image permanence. The heat-sensitive recording materials based on these colour developers also have a usable thermal sensitivity with good surface whiteness, such that, with appropriate composition of the formulation of the heat-sensitive colour-forming layer, it is relatively easy to produce high print densities with use of commercially available thermal printers.

WO 0 035 679 A1 discloses aromatic and heteroaromatic sulfonyl-(thio)urea compounds (X=S or O) and/or sulfonyl guanidines (X=NH) of formula

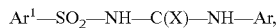

wherein Ar is linked to further aromatic groups by a divalent linker group. A non-phenolic developer from this class that is widely used in practice, 4-methyl-N-(((3-(((4-methylphenyl)sulfonyl)oxy)phenyl)amino) carbonyl)benzenesulfonamide (trade name Pergafast 201®, BASF), is characterised by the balance of the application properties. Especially, they have a good dynamic response sensitivity and a high resistance of the print to hydrophobic substances in comparison to recording materials obtained using (bis)phenolic colour developers. Any new products must be measured against the performance spectrum of this established non-phenolic colour developer.

Sulfonyl ureas tend towards hydrolytic decomposition reactions in the presence of water or moisture and under heat. This means that heat-sensitive recording materials may experience a partial decomposition of the colour developer when stored in the unprinted state in conditions of increased air humidity and/or temperature.

Since the writing performance (dynamic response sensitivity) of heat-sensitive recording materials is also dependent on the amount of colour developer present in the heat-sensitive layer, a heat-sensitive recording material stored in this way over longer periods of time loses some of the colour developer and thus some of its writing performance.

The above-mentioned possibility of modulating the properties of the 1,3'-disubstituted urea unit can also be achieved by incorporating groups that are not bonded to the ureido unit directly, but via a linker group, whether in the conjugative compound unit or located in the synergistically advantageous position.

This approach was followed for example in JP H 11 268 421. This discloses the combination of a (thio)ureido unit with a sulfamoyl group (—NH—SO$_2$—) of formula

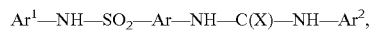

wherein Ar, Ar$^1$ and Ar$^2$ are mononuclear aromatic groups and X=S or O.

JP 11 268 422 A discloses structures of formula

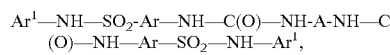

wherein A can be aromatic or aliphatic groups. Structures with primary —SO$_2$—NH$_2$— groups are described in this context (EP 0 693 386 A1).

EP 2 923 851 A1 discloses colour developer structures of formula

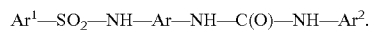

Although heat-sensitive recording materials based on these colour developers ensure good dynamic sensitivity, the stability of the colour complex, especially with respect to plasticisers or adhesives, is in need of improvement.

Even early on, attempts were made to improve the performance of non-phenolic colour developers by use of colour developer structures that contain more than just one structural unit relevant for the colour-forming process.

JP H 06 227 142 A discloses colour developers having two, three or more (thio)urea units (bis-, tris-, polykis-ureas) in the compound (Ar$^1$—NH—C(X)—NH)$_n$-A, which are bonded to a usually aromatic unit A (X=S or O).

The colour developers described in EP 633 145 A1, JP H 082 109 A, JP H 08 244 355 A, JP H 8/244,355 A and JP H 11 268 422 A are similarly structured.

This approach has been widely varied by the use of —OH, —CO$_2$H, —SO$_2$NH$_2$ and —SO$_2$NH aryl-group-substituted Ar$^1$ groups (JP H 082 109 A, JP H 08 244 355 A, JP 08 197 851 A, JP H 10 230 681 A, JP H 11 268 422 A).

Although bis- or polykis-urea derivatives have good H-bridge acceptor and donor properties and are therefore suitable for stabilising the colour complex, the hydrogen bridge networks forming between the individual urea units are responsible for a relatively high melting point and a low solubility of these substances in typical thermal solvents from the heat-sensitive layer, with the result that the thermal response sensitivity (what is known as dynamic sensitivity) of the heat-sensitive recording materials produced with use of these colour developers is lacking.

The aim of the present invention is therefore to overcome the above-described disadvantages of the prior art. Especially, the aim of the present invention is to provide a colour developer and a heat-sensitive recording material containing same, which recording material has a balanced application property profile and achieves a practicable print density, comparable to that possible with established, non-phenolic colour developers of the prior art, but ensures a high resistance of the printed image, especially with respect to hydrophobic agents, without being reliant on specific formulation components in the heat-sensitive functional layer, such as ageing inhibitors or specific melt auxiliaries, which have limited availability and are costly. A further aim of the present invention is to provide a heat-sensitive recording material that is able to ensure the functional properties necessary for the particular application (especially the thermal response sensitivity), also under conditions of storage over long periods of time under extreme climatic conditions of the unprinted material.

This aim is addressed in accordance with the invention by the use of a compound according to claim 1 in a heat-sensitive recording material according to claim 13.

The compound according to claim 1 has the formula (I)

$$Ar(NHSO_2Ar^1)_l(SO_2NHAr^1)_m(NHC(O)NHAr^2)_n \qquad (I),$$

wherein l and m independently of one another are 0, 1, 2, 3 and/or 4 and the sum of l+m is equal to or greater than 1, n is 2, 3, 4 or 5, Ar is benzene group substituted (l+m+n) times, $Ar^1$ is an unsubstituted or substituted aromatic group, and $Ar^2$ is an unsubstituted or substituted phenyl group or a benzoyl group.

The sum of l+m is preferably 1 or 2 and very especially preferably 1, since compounds of this kind are more easily accessible synthetically.

Preferably, l or m is 0, since compounds of this kind are more easily accessible synthetically.

Preferably l is 0 or 1, especially preferably 1, since compounds of this kind are more easily accessible synthetically.

Preferably m is 0, 1 or 2, preferably 0 or 1 and especially preferably 0, since compounds of this kind are more easily accessible synthetically.

Preferably n is 2, since compounds of this kind are more easily accessible synthetically.

A compound of formula (I), wherein l is 1, m is 0 and n is 2 is especially preferred.

A compound of formula (I), wherein l is 0, m is 1 and n is 2 is likewise especially preferred.

A compound of formula (I), wherein l is 0, m is 2 and n is 2 is also especially preferred.

Ar is preferably a benzene group substituted 3 or 4 times.

As already mentioned, $Ar^1$ is an unsubstituted or substituted aromatic group. The substitution can be a mono- or polysubstitution with the same or different groups. The unsubstituted or substituted aromatic group is preferably a phenyl group or a 4-alkoxy carbonyl phenyl group. In a especially preferred embodiment the phenyl group is a monosubstituted phenyl group. Compounds of this kind have, the advantage that they are more easily accessible synthetically.

The monosubstituted phenyl group is preferably substituted with a $C_1$-$C_5$ alkyl, an alkenyl, an alkynyl, a benzyl, an RO, a halogen, formyl, an ROC, an $RO_2C$, a CN, an $NO_2$, an R—$SO_2O$, an RO—$SO_2$, an R—NH—$SO_2$, an R—$SO_2$—NH, an R—NH—CO—NH, an R—$SO_2$—NH—CO—NH, an R—NH—CO—NH—R or an R—CO—NH group, wherein R is a $C_1$-$C_5$ alkyl, an alkenyl, an alkynyl, a phenyl, a tolyl or a benzyl group.

The monosubstituted phenyl group is very especially preferably substituted with a 4-$C_1$-$C_5$ alkyl, preferably a 4-methyl, 4-ethyl, 4-n-propyl or 4-iso-propyl group, a 4-RO or a 4-($RO_2C$) group, wherein R is a $C_1$ to $C_5$ alkyl group, preferably a methyl or an ethyl group.

Especially preferably Ar¹ is a phenyl or a 4-tolyl group, since compounds of this kind are more easily accessible synthetically.

As mentioned above, $Ar^2$ is an unsubstituted or substituted phenyl group or a benzoyl group. These are preferably substituted with a $C_1$ to $C_4$ alkyl, a halogen, a $CX_3$, a formyl, an ROC, an $RO_2C$, a CN, an $NO_2$ or an RO group, wherein X is a halogen group and R is a $C_1$ to $C_5$ alkyl group, preferably a methyl group, a phenyl group or a tolyl group.

$Ar^2$ is especially preferably a phenyl, a 4-tolyl, or a 4-acetyl phenyl group. This has the advantage that the application properties, especially the resistance to plasticiser, are very good.

Especially preferred individual compounds of formula (I) are shown in the following Table 1.

| Ar | Ar¹ | Ar² | l | m | n |
|---|---|---|---|---|---|
| benzene-triyl | phenyl | phenyl | 1 | 0 | 2 |
| benzene-triyl | phenyl | phenyl | 0 | 1 | 2 |
| benzene-triyl | monosubstituted phenyl | phenyl | 1 | 0 | 2 |
| benzene-triyl | $C_1$-$C_5$ alkyl-substituted phenyl | phenyl | 1 | 0 | 2 |
| benzene-triyl | monosubstituted phenyl | RO-substituted phenyl | 1 | 0 | 2 |
| benzene-triyl | $C_1$-$C_5$ alkyl-substituted phenyl | RO-substituted phenyl | 1 | 0 | 2 |
| benzene-triyl | $C_1$-$C_5$ alkyl-substituted phenyl | $C_1$-$C_4$ alkyl-substituted phenyl | 1 | 0 | 2 |
| benzene-triyl | $C_1$-$C_5$ alkyl-substituted phenyl | PhO-substituted phenyl | 1 | 0 | 2 |
| benzene-triyl | $C_1$-$C_5$ alkyl-substituted phenyl | halogen-substituted phenyl | 1 | 0 | 2 |
| benzene-triyl | $C_1$-$C_5$ alkyl-substituted phenyl | $CX_3$-substituted phenyl | 1 | 0 | 2 |
| benzene-triyl | halogen-substituted phenyl | phenyl | 1 | 0 | 2 |
| benzene-triyl | RO-substituted phenyl | phenyl | 1 | 0 | 2 |
| benzene-triyl | $C_1$-$C_5$ alkyl-substituted phenyl | ROC-substituted phenyl | 1 | 0 | 2 |
| benzene-triyl | $C_1$-$C_5$ alkyl-substituted phenyl | benzoyl- | 1 | 0 | 2 |
| benzene-triyl | $RO_2C$-substituted phenyl | phenyl | 0 | 1 | 2 |

-continued

| Ar | Ar$^1$ | Ar$^2$ | l | m | n |
|---|---|---|---|---|---|
| benzene-tetryl | phenyl | phenyl | 0 | 2 | 2 |

Table 1: Preferred compounds of formula (I) with the stated meanings for the groups Ar, Ar$^1$ and Ar$^2$ and for the indices 1, m and n A benzoyl-triyl group is understood to mean triple substituted benzene group, and a benzoyl-tetryl group is understood to mean a quadruple substituted benzene group. The triple substitution is performed preferably at positions 1, 2 and 3, 1, 2 and 4, 1, 2 and 5, 1, 2 and 6 or 1, 3 and 4. The quadruple substitution is preferably performed at positions 1, 3, 4 and 6.

In Table 1 above, R preferably means a $C_1$-$C_4$ alkyl group and X means a halogen group, especially preferably a fluoride group.

The compound of formula (I) according to the invention can be produced by means known per se.

The following reaction scheme 1 shows a possible synthesis pathway for the compound of formula (I) according to the invention on the basis of the example of compounds I to XVIII (see Table 2).

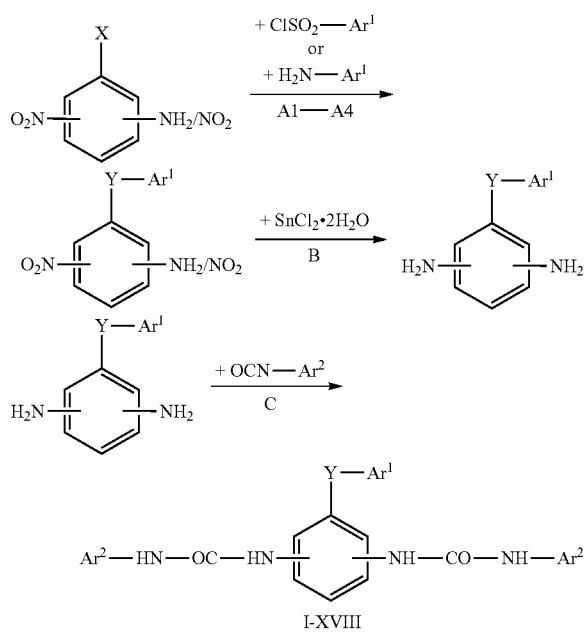

Reaction scheme 1 (Ar$^1$, Ar$^2$: see Table 2; X=NH$_2$ (I-XVI) or SO$_2$Cl (XVII-XVIII); Y=NHSO$_2$ (I-XVI) or SO$_2$NH (XVII-XVIII))

The compounds I and II falling under the compound of formula (I) according to the invention (see Table 2) can be produced starting from 2,6-dinitroaniline, which is firstly converted in accordance with the following reaction scheme 2 into 1,2-diamino-3-nitrobenzene (V. Milata, J. Salon, Org. Prep. Proceed. Int., 31 (3), 347 (1999)).

Reaction scheme 2

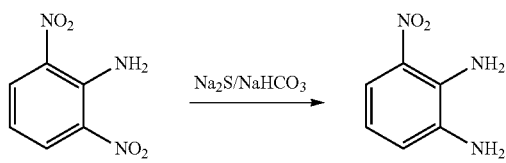

The compound XIX falling under the compound of formula (I) according to the invention (see Table 2) can be produced starting from 1,3-phenylenediamine dihydrochloride, which is firstly converted in accordance with the following reaction scheme 3 into the corresponding bis-amino sulfonyl chloride (G. Barnikow, K. Krüger, G. Hilgetag, Z. Chem., 6 (7), 262 (1966)) and is then converted into the end product by the described methods.

Reaction scheme 3

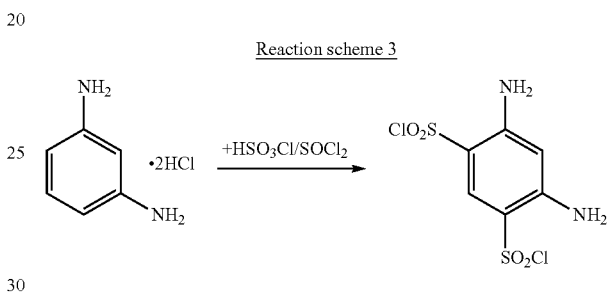

As already mentioned, the present invention also relates to a heat-sensitive recording material comprising a carrier substrate, at least one colour former, and at least one heat-sensitive colour-forming layer containing phenol-free colour developer, wherein the at least one phenol-free colour developer is the compound of the above-mentioned formula (I).

The compound of formula (I) is preferably present in an amount of from approximately 3 to approximately 35% by weight, especially preferably in an amount of from approximately 10 to approximately 25% by weight, in relation to the total solid content of the heat-sensitive layer.

The selection of the carrier substrate is not critical. However, it is preferred to use paper, synthetic paper, and/or a plastic film as carrier substrate.

At least one further intermediate layer is optionally provided between the carrier substrate and the heat-sensitive layer, wherein the purpose of this at least one further intermediate layer is to improve the surface smoothness of the carrier for the heat-sensitive layer and to ensure a heat barrier between the carrier substrate and the heat-sensitive layer.

Organic hollow bead pigments and/or calcined kaolins are preferably used in this intermediate layer.

At least one protective layer arranged above the heat-sensitive layer and/or at least one layer promoting printability can also be provided in the heat-sensitive recording material according to the invention, wherein these layers can be applied on the front or rear side of the substrate.

With regard to the choice of the colour former, the present invention is also not subject to any major limitations. The colour former, however, is preferably a dye of the triphenyl-methane type, of the fluorane type, of the azaphthalide type and/or of the fluorene type. A very especially preferred colour former is a dye of the fluorane type, since, thanks to its availability and balanced application-related properties, it is possible to provide a recording material having an attractive price-performance ratio.

Especially preferred dyes of the fluorane type are:
3-diethylamino-6-methyl-7-anilinofluorane,
3-(N-ethyl-N-p-toluidineamino)-6-methyl-7-anilinofluorane,
3-(N-ethyl-N-isoamylamino)-6-methyl-7-anilinofluorane,
3-diethylamino-6-methyl-7-(o,p-dimethylanilino)fluorane,
3-pyrrolidino-6-methyl-7-anilinofluorane,
3-(cyclohexyl-N-methylamino)-6-methyl-7-anilinofluorane,
3-diethylamino-7-(m-trifluoromethylanilino)fluorane,
3-N-n-dibutylamino-6-methyl-7-anilinofluorane,
3-diethylamino-6-methyl-7-(m-methylanilino)fluorane,
3-N-n-dibutylamino-7-(o-chloroanilino) fluorane,
3-(N-ethyl-N-tetrahydrofurfurylamine)-6-methyl-7-anilino-fluorane,
3-(N-methyl-N-propylamine)-6-methyl-7-anilinofluorane,
3-(N-ethyl-N-ethoxypropylamine)-6-methyl-7-anilinofluorane,
3-(N-ethyl-N-isobutylamine)-6-methyl-7-anilinofluorane and/or
3-dipentylamine-6-methyl-7-anilinofluorane.

The colour formers can be used as individual substances or as any mixtures of two or more colour formers, provided that the desirable application properties of the recording materials are not compromised.

The colour former is preferably present in an amount of from approximately 5 to approximately 30, especially preferably in an amount of from approximately 8 to approximately 20, in relation to the total solid content of the heat-sensitive layer.

In order to control specific application properties, it can be advantageous if at least two of the compounds corresponding to general formula (I) are present as colour developer in the heat-sensitive layer.

Likewise, one or more further (bis)phenolic or non-phenolic colour developers can be present in the heat-sensitive colour-forming layer in addition to compounds of formula (I).

Besides the at least one colour former and the at least one colour developer, one or more sensitisation agents, also referred to as thermal solvents or melt auxiliaries, can be present in the heat-sensitive colour-forming layer, which has the advantage that the thermal print sensitivity can be controlled more easily.

Crystalline substances of which the melting point is between approximately 90 and approximately 150° C. and which in the molten state dissolve the colour-forming components (colour former and colour developer) without interfering with the formation of the colour complex are generally considered to be advantageous sensitisation agents.

The sensitisation agent is preferably a fatty acid amide, such as stearamide, behenamide or palmitamide, an ethylene-bis-fatty acid amide, such as N,N'-ethylene-bis-stearic acid amide or N,N'-ethylene-bis-oleic acid amide, a fatty acid alanolamide, such as N-(hydroxymethyl) stearamide, N-hydroxymethylpalmitamide or hydroxyethylstearamide, a wax, such as polyethylene wax or montan wax, a carboxylic acid ester, such as dimethyl terephthalate, dibenzyl terephthalate, benzyl-4-benzyloxy benzoate, di-(4-methylbenzyl) oxalate, di-(4-chlorbenzyl)oxalate or di-(4-benzyl)oxalate, ketones, such as 4-acetylbiphenyl, an aromatic ether, such as 1,2-diphenoxyethane, 1,2-di-(3-methylphenoxy)ethane, 2-benzyloxynaphthalene, 1,2-bis-(phenoxymethyl)benzene or 1,4-diethoxynaphthalene, an aromatic sulfone, such as diphenylsulfone, and/or an aromatic sulfonamide, such as 4-toluenesulfonamide, benzene sulfonamide or N-benzyl-4-toluolenesulfonamide or aromatic hydrocarbons, such as 4-benzylbiphenyl.

The sensitisation agent is preferably present in an amount of from approximately 10 to approximately 40, especially preferably in an amount of from approximately 15 to approximately 25, in relation to the total solid content of the heat-sensitive layer.

In a further preferred embodiment, besides the colour former, the phenol-free colour developer and the sensitisation agent, optionally at least one stabiliser (ageing inhibitor) is present in the heat-sensitive colour-forming layer.

The stabiliser is preferably constituted by sterically hindered phenols, especially preferably by 1,1,3-tris-(2-methyl-4-hydroxy-5-cyclohexyl-phenyl)butane, 1,1,3-tris-(2-methyl-4-hydroxy-5-tert-butylphenyl)butane, 1,1-bis-(2-methyl-4-hydroxy-5-tert-butyl-phenyl)butane.

Urea-urethane compounds (commercial product UU) or 4,4'-dihydroxydiphenylsulfone-derived ethers, such as 4-benzyloxy-4'-(2-methylglycidyloxy)-diphenylsulfone (trade name NTZ-95®, Nippon Soda Co. Ltd.), or oligomeric ethers (trade name D90®, Nippon Soda Co. Ltd.) are also usable as stabilisers in the recording material according to the invention.

The stabiliser is preferably present in an amount of from 0.2 to 0.5 parts by weight, in relation to the at least one phenol-free colour developer of the compound of formula (I).

In a further preferred embodiment at least one binder is present in the heat-sensitive colour-forming layer. This binder is preferably constituted by water-soluble starches, starch derivatives, starch-based biolatices of the EcoSphere® type, methyl cellulose, hydroxyethyl cellulose, carboxymethyl cellulose, partially or fully saponified polyvinyl alcohols, chemically modified polyvinyl alcohols or styrene-maleic acid anhydride copolymers, styrene-butadiene copolymers, acrylamide-meth)acrylate copolymers, acrylamide-acrylate-methacrylate terpolymers, polyacrylates, poly(meth)acrylic esters, acrylate-butadiene copolymers, polyvinyl acetates and/or acrylonitrile-butadiene copolymers.

In a further preferred embodiment at least one separating agent (release agent) or slip additive is present in the heat-sensitive colour-forming layer. These agents are preferably fatty acid metal salts, such as zinc stearate or calcium stearate, or also behenate salts, synthetic wax, for example in the form of fatty acid amides, such as stearic acid amide and behenic acid amide, fatty acid alkanolamides, such as stearic acid methylolamide, paraffin waxes having different melting points, ester waxes of different molecular weights, ethylene waxes, propylene waxes of different hardnesses and/or natural waxes, such as carnauba wax or montan wax.

The separating agent is preferably present in an amount of from approximately to approximately 10, especially preferably in an amount of from approximately 3 to approximately 6, in relation to the total solid content of the heat-sensitive layer.

In a further preferred embodiment the heat-sensitive colour-forming layer contains pigments. The use of these has the advantage, inter alia, that they can fix the chemical melt created in the thermal printing process on their surface. The surface whiteness and opacity of the heat-sensitive colour-forming layer and printability thereof with conventional printing inks can also be controlled via pigments. Lastly, pigments have an "extender function", for example for the relatively expensive colour-giving functional chemicals.

Especially suitable pigments are inorganic pigments, both or synthetic and natural origin, preferably clays, precipitated or natural calcium carbonates, aluminium oxides, aluminium hydroxides, silicas, precipitated and pyrogenic silicas (for example Aerodisp® types), diatomaceous earths, magnesium carbonates, talc, but also organic pigments, such as hollow pigments with a styrene/acrylate copolymer wall or urea/formaldehyde condensation polymers. These can be used alone or in any mixtures.

The pigments are preferably present in an amount of from approximately 20 to approximately 50, especially preferably in an amount of from approximately 30 to approximately 40, in relation to the total solid content of the heat-sensitive layer.

In order to control the surface whiteness of the heat-sensitive recording material according to the invention, optical brighteners can be incorporated into the heat-sensitive colour-forming layer. These are preferably stilbenes.

In order to improve certain coating properties, it is preferred in individual cases to add further constituents, especially rheology aids, such as thickeners and/or surfactants, to the mandatory constituents of the heat-sensitive recording material according to the invention.

The area application weight of the (dry) heat-sensitive layer is preferably approximately 1 to approximately 10 g/m$^2$, preferably approximately 3 to approximately 6 g/m$^2$.

In an especially preferred embodiment the heat-sensitive recording material is one according to claim 13, wherein a dye of the fluorane type is used as colour former, and a sensitisation means, selected from the group consisting of fatty acid amides, aromatic sulfones and/or aromatic ethers, is additionally present. In this preferred embodiment it is also advantageous that approximately 1.5 to approximately 4 parts by weight of the phenol-free colour developer according to claim 1 are present, in relation to the colour former.

The preferred embodiments described in conjunction with the compound of formula (I) are also applicable for the heat-sensitive recording material according to the invention.

The heat-sensitive recording material according to the invention can be obtained by means of known production methods.

It is advantageous if the dried heat-sensitive colour-forming layer is subjected to a smoothing measure. Here, it is advantageous if the Bekk smoothness, measured in accordance with ISO 5627:1995-03, is set to approximately 100 to approximately 1000 sec., preferably to approximately 250 to approximately 600 sec.

The surface roughness (PPS) according to ISO 8791-4: 2008-05 lies in the range of from approximately 0.50 to approximately 2.50 μm, preferably in the range of from 1.00 to 2.00 μm.

The heat-sensitive recording material according to the invention is phenol-free and well suited for POS (point-of-sale), labelling and/or ticketing applications. It is also suitable for the production of parking tickets, travel tickets, entry cards, and lottery and betting slips, etc., which can be printed in direct thermal printing and require a high resistance of the images recorded thereon under longer-term storage, even under harsher climatic conditions in respect of temperature and ambient moisture, and in the event that the printed text is brought into contact with hydrophobic substances, such as plasticisers, adhesives, greasy or oily substances, etc.

The heat-sensitive recording materials obtained with the developers of formula (I) according to the invention hardly experience any reduction in their capability to produce high image densities, even after storage over several weeks of the unprinted materials at high ambient air humidity and temperature (good suitability for storage).

To summarise it can be said that it has been surprisingly demonstrated that it is possible to obtain, with the colour developers of formula (I) according to the invention, heat-sensitive recording materials which are characterised by excellent resistance of the printed text to hydrophobic agents and with which a good quality of the printed image (high optical density of the printed image) can be achieved. Furthermore, the suitability for long-term storage of the heat-sensitive recording materials according to the invention is excellent. Even if stored in the unprinted state for several weeks at high ambient humidities or temperatures, the attained optical density hardly suffers during printing in a thermal printer.

Without being linked to this theory, especially the molecular arrangement in close vicinity of an increased number (≥3) of functional groups essential for the colour-forming and colour-stabilising process (high molecular density of the significant functional groups) directly at one and the same aromatic unit corresponding to general formula (I) appears to play an important role.

The invention will be explained in detail hereinafter on the basis of non-exhaustive examples.

Non-phenolic colour developers from the prior art were used as comparison developers: Two isomeric urea derivatives with N-phenyl-2-(3-phenyl-ureido-benzenesulfonamide (Y) and N-(2-(3-phenylureido)phenyl)benzenesulfonamide (Z) and a sulfonyl urea with Pergafast 201®, BASF (PF201).

EXAMPLES

Production of the compounds of formula (I) according to the invention.

The compounds I to XIX (Table 2) were produced as follows:

Step A1—Preparation of the Sulfonamides

A solution of 10 mmol of the corresponding sulfonyl chloride in 75 mL dichloromethane was added dropwise to a solution of 20 mmol aromatic diamine and 20 mmol pyridine in 125 mL dichloromethane at 0° C. under stirring. The reaction solution was stirred for 16 hours at room temperature, before 100 mL water were added. The organic phase was separated and mixed with 250 mL of a 5% aqueous sodium hydroxide solution. The aqueous phase was washed with 100 mL dichloromethane and made neutral by adding 25% hydrochloric acid. After multiple extractions with 100 mL dichloromethane, the combined organic phases were washed with 200 mL water and dried over magnesium sulfate. Following removal of the solvent in a vacuum the sulfonamides were used in step B without further purification.

Step A2—Preparation of the Sulfonamides

A solution of 80 mmol of the corresponding sulfonyl chloride in 150 mL dichloromethane was added dropwise to a solution of 80 mmol aromatic diamine and 240 mmol potassium carbonate in 500 mL dichloromethane at room temperature under stirring. The reaction mixture was refluxed for six hours, and then 300 mL ethyl acetate and 300 mL water were added. The aqueous phase was made acidic by adding 25% hydrochloric acid. The phases were separated. After multiple extractions of the aqueous phase with 200 mL ethyl acetate, the combined organic phases were washed with 200 mL water and dried over magnesium sulfate. Following removal of the solvent in a vacuum the sulfonamide remained as a solid. The sulfonamides were used in step B without further purification.

Step A3—Preparation of the Sulfonamides

A solution of 25.0 mmol of aromatic amine in 35 mL abs. THF was added dropwise to a solution of 27.5 mmol sodium hydride (60% in oil) in 25 mL abs. THF at 0° C. under stirring and protective gas atmosphere. After stirring for two hours at room temperature, a solution of 25.0 mmol of the corresponding sulfonyl chloride in 10 mL abs. THF was added dropwise at 0° C. under stirring. The reaction solution was stirred for 40 hours at room temperature, and then 100 mL water and 100 mL dichloromethane were added. The aqueous phase was made alkaline by adding 5% aqueous sodium hydroxide solution. The phases were separated. The aqueous phase was washed with 100 mL dichloromethane and was made neutral by adding 15% hydrochloric acid. After multiple extractions with 100 mL dichloromethane, the combined organic phases were washed with 200 mL water and dried over magnesium sulfate. Following removal of the solvent in a vacuum the sulfonamide remained as a solid. The sulfonamides were used in step B without further purification.

Step A4—Preparation of the Sulfonamides 50 mmol of the corresponding sulfonyl chloride were added in portions to a mixture of 55 mmol aromatic amine and 50 mmol pyridine under stirring. The mixture was heated briefly (5-10 min) to 95-100° C., cooled, and rubbed with 100-150 mL hydrochloric acid (2 mol/L). The precipitating sulphonamide was filtered off, washed neutral with water, and dried. The sulfonamides were used in step B without further purification.

Step B—Reduction of the Nitro Group to Give the Primary Amine 28.0 mmol (products from step A1) or 56.0 mmol (products from steps A2/A3/A4) $SnCl_2.2H_2O$ were added to a solution of 8.0 mmol of the product from step A1/A2/A3/A4 in 140 mL ethyl acetate at room temperature under stirring. The reaction solution was refluxed. The course of the reaction was monitored by means of thin-film chromatography (eluents: cyclohexane/ethyl acetate 1:1). Once the reaction was complete (approximately 2-3 h), the mixture was diluted with 70 mL ethyl acetate, a 10% aqueous potassium carbonate solution was added, and the mixture was stirred for 30 min at room temperature. The Sn compounds were filtered off and in the filtrate the aqueous phase was separated from the organic phase. The organic phase was washed with 100 ml (2×) of a saturated aqueous sodium chloride solution and dried over magnesium sulfate. Following removal of the solvent in a vacuum, purification was performed by recrystallisation from dichloromethane and a few drops of n-hexane.

Step C—Preparation of the Urea Compounds

A solution of 14.0 mmol of the corresponding isocyanate in 10 mL dichloromethane (I-XVIII) or ethyl acetate (XIX) was added dropwise to a solution of 7.0 mmol of the product from step B in dichloromethane (I-XVIII) or ethyl acetate (XIX) (20-40 mL) at room temperature under stirring. The reaction was monitored by means of thin-film chromatography (eluents: cyclohexane/ethyl acetate 1:1). Once the reaction was complete, the precipitated product was filtered off, washed with dichloromethane/ethyl acetate, and dried in a vacuum. In some cases the reaction solution was concentrated in the vacuum and the crystallisation was initiated by adding a few drops of n-hexane.

The compounds I-II (Table 2) were prepared starting from 2,6-dinitroaniline, which was firstly converted into 1,2-diamino-3-nitrobenzene (reaction scheme 2, V. Milata, J. Saloň, Org. Prep. Proceed. Int., 31 (3), 347 (1999)) and finally was converted into the end product in accordance with the general provisions of steps A1, B and C.

The compounds III-XVI (Table 2) were prepared starting from 2,6-dinitroaniline (III), 4-nitro-1,2-phenylenediamine (IV), 2,6-dinitroaniline (V) and 2-nitro-1,4-phenylenediamine (VI-XVI) were prepared in accordance with the general provisions of steps A1 (IV, VI-XVI), A2 (III), A3 (V), B (III-XVI) and C (III-XVI).

The compounds XVII-XVIII (Table 2) were prepared starting from 2,4-dinitrosulfonylchloride in accordance with the general provisions of steps A4, B and C.

The compound XIX (Table 2) was prepared starting from 1,3-phenylenediamine-dihydrochloride, which was firstly converted into 4,6-diamino-1,3-benzenedisulfonyl chloride (reaction scheme 3, G. Barnikow, K. Krüger, G. Hilgetag, Z. Chem., 6(7), 262 (1966)) and finally was converted into the end product in accordance with the general provisions of steps A4 and C.

The starting compounds are commercially available.

TABLE 2

Compilation of selected compounds of formula (I)

| | Ar | $Ar^1$ | $Ar^2$ | l | m | n |
|---|---|---|---|---|---|---|
| I | benzene-1,2,3-triyl | 4-$CH_3$—$C_6H_4$ | $C_6H_5$ | 1 | 0 | 2 |
| II | benzene-1,2,3-triyl | 4-$CH_3$—$C_6H_4$ | 4-(CO—$CH_3$)—$C_6H_4$ | 1 | 0 | 2 |
| III | benzene-1,2,3-triyl | 4-$CH_3$—$C_6H_4$ | $C_6H_5$ | 1 | 0 | 2 |
| IV | benzene-1,2,3-triyl | 4-$CH_3$—$C_6H_4$ | $C_6H_5$ | 1 | 0 | 2 |
| V | benzene-1,2,3-triyl | 4-$CH_3$—$C_6H_4$ | $C_6H_5$ | 1 | 0 | 2 |
| VI | benzene-1,2,3-triyl | $C_6H_5$ | $C_6H_5$ | 1 | 0 | 2 |
| VII | benzene-1,2,3-triyl | 4-$CH_3$—$C_6H_4$ | $C_6H_5$ | 1 | 0 | 2 |
| VIII | benzene-1,2,3-triyl | 4-Cl—$C_6H_4$ | $C_6H_5$ | 1 | 0 | 2 |
| IX | benzene-1,2,3-triyl | 4-$OCH_3C_6H_4$ | $C_6H_5$ | 1 | 0 | 2 |
| X | benzene-1,2,3-triyl | 4-$CH_3$—$C_6H_4$ | 4-$CH_3$—$C_6H_4$ | 1 | 0 | 2 |
| XI | benzene-1,2,3-triyl | 4-$CH_3$—$C_6H_4$ | 4-$OCH_3$—$C_6H_4$ | 1 | 0 | 2 |
| XII | benzene-1,2,3-triyl | 4-$CH_3$—$C_6H_4$ | 4-$OC_6H_5$—$C_6H_4$ | 1 | 0 | 2 |
| XIII | benzene-1,2,3-triyl | 4-$CH_3$—$C_6H_4$ | 4-Cl—$C_6H_4$ | 1 | 0 | 2 |
| XIV | benzene-1,2,3-triyl | 4-$CH_3$—$C_6H_4$ | 4 (CO—$CH_3$)—$C_6H_4$ | 1 | 0 | 2 |
| XV | benzene-1,2,3-triyl | 4-$CH_3$—$C_6H_4$ | 2-$CF_3$—$C_6H_4$ | 1 | 0 | 2 |
| XVI | benzene-1,2,3-triyl | 4-$CH_3$—$C_6H_4$ | CO—$C_6H_4$ | 1 | 0 | 2 |

TABLE 2-continued

Compilation of selected compounds of formula (I)

| | Ar | Ar$^1$ | Ar$^2$ | l | m | n |
|---|---|---|---|---|---|---|
| XVII | benzene-1,2,3-triyl | C$_6$H$_5$ | C$_6$H$_5$ | 0 | 1 | 2 |
| XVIII | benzene-1,2,3-triyl | 4-(CO$_2$C$_2$H$_5$)—C$_6$H$_5$ | C$_6$H$_5$ | 0 | 1 | 2 |
| XIX | benzene-1,2,3-tetryl | C$_6$H$_5$ | C$_6$H$_5$ | 0 | 2 | 2 |

Analytical data:

I, C$_{27}$H$_{25}$N$_3$O$_4$S, M=515.6, N-(2,3-bis(3-phenylureide)phenyl)tosylamide MS (ESI): m/z (%)=514.0 (76) [M–H]–, 395.0 (16) [M–H—Ar$^2$NCO]–.

$^1$H-NMR (500 MHz, DMSO-d$_6$): δ (ppm)=9.47 (1H, s), 9.34 (1H, s), 9.23 (1H, s), 8.06 (1H, s), 7.80-7.78 (1H, m), 7.70 (1H, s), 7.64-7.63 (2H, m), 7.54-7.52 (2H, m), 7.48-7.46 (2H, m), 7.33-7.25 (6H, m), 7.09-7.05 (1H, m), 7.01-6.98 (1H, m), 6.97-6.94 (1H, m), 6.63-6.61 (1H, m), 2.33 (3H, s).

$^{13}$C-NMR (126 MHz, DMSO-d$_6$): δ (ppm)=153.66 (NHCONH), 152.61 (NHCONH), 143.14, 139.89, 139.73, 136.92, 136.81, 132.89, 129.53, 128.69, 128.68, 126.76, 125.85, 124.38, 121.80, 121.76, 119.98, 119.17, 118.28, 118.22, 20.95 (CH$_3$).

II, C$_{31}$H$_{29}$N$_5$O$_6$S, M=599.7, N-(2,3-bis(3-(4-acetylphenyl)ureido)phenyl)tosylamide MS (ESI): m/z (%)=598.1 (100) [M–H]–.

$^1$H-NMR (500 MHz, DMSO-d$_6$): δ (ppm)=9.74 (1H, s), 9.65 (1H, s), 9.52 (1H, s), 8.14 (1H, s), 7.95-7.94 (2H, m), 7.90-7.88 (2H, m), 7.80-7.78 (2H, m), 7.64-7.62 (4H, m), 7.58-7.57 (2H, m), 7.32-7.31 (2H, m), 7.11-7.08 (1H, m), 6.62-6.61 (1H, m), 2.53 (3H, s), 2.50 (3H, s), 2.33 (3H, s).

$^{13}$C-NMR (126 MHz, DMSO-d$_6$): δ (ppm)=196.17 (COCH$_3$), 196.13 (COCH$_3$), 153.19 (NHCONH), 152.20 (NHCONH), 144.50, 144.28, 143.14, 136.81, 136.61, 133.13, 130.46, 130.41, 129.52, 129.52, 129.50, 126.75, 126.19, 124.13, 120.00, 119.42, 117.16, 117.16, 26.21 (CH$_3$), 26.18 (CH$_3$), 20.91 (CH$_3$).

III, C$_{27}$H$_{25}$N$_5$O$_4$S, M=515.6, N-(2,4-bis(3-phenylureido)phenyl)tosylamide MS (ESI): m/z (%)=514.1 (100) [M–H]–

$^1$H-NMR (500 MHz, DMSO-d$_6$): δ (ppm)=9.54 (1H, s), 9.27 (1H, s), 8.78 (1H, s), 8.53 (1H, s), 8.28 (1H, s), 8.15 (1H, d, J=2.2 Hz), 7.61-7.60 (2H, m), 7.53-7.52 (2H, m), 7.46-7.44 (2H, m), 7.36-7.34 (2H, m), 7.33-7.30 (2H, m), 7.29-7.26 (2H, m), 7.08 (1H, dd, 8.7, 2.2 Hz), 7.01-6.95 (2H, m), 6.39 (1H, d, 8.6 Hz), 2.34 (3H, s).

$^{13}$C-NMR (126 MHz, DMSO-dd: δ (ppm)=152.35 (NHCONH), 152.31 (NHCONH), 143.16, 139.84, 139.54, 139.23, 137.78, 136.48, 129.43, 128.78, 128.74, 128.15, 127.26, 121.87, 121.84, 118.38, 118.19, 118.17, 111.23, 109.79, 20.97 (CH$_3$).

IV, C$_{27}$H$_{25}$N$_5$O$_4$S, M=515.6, N-(2,5-bis(3-phenylureido)phenyl)tosylamide MS (ESI): m/z (%)=514.0 (100) [M–H]$^-$ $^1$H-NMR (500 MHz, DMSO-d$_6$): δ (ppm)=9.47 (1H, s), 9.23 (1H, s), 8.54 (1H, s), 8.49 (1H, s), 8.06 (1H, s), 7.73 (1H, d, J=8.7 Hz), 7.65-7.63 (2H, m), 7.50-7.48 (2H, m), 7.45-7.43 (2H, m), 7.34-7.26 (7H, m), 7.01 (1H, d, 3=2.2 Hz), 6.99-6.95 (2H, m), 2.31 (3H, s).

$^{13}$C-NMR (126 MHz, DMSO-d$_6$): δ (ppm)=152.84 (NHCONH), 152.25 (NHCONH), 143.15, 139.92, 139.65, 136.60, 134.86, 129.68, 129.49, 128.73, 128.72, 127.01, 126.78, 122.72, 121.76, 121.70, 118.16, 118.12, 117.01, 116.51, 20.97 (CH$_3$).

V, C$_{27}$H$_{25}$N$_5$O$_4$S, M=515.6, N-(2,6-bis(3-phenylureido)phenyl)tosylamide MS (ESI): m/z (%)=514.1 (100) [M–H]$^-$.

$^1$H-NMR (500 MHz, DMSO-d$_6$): δ (ppm)=8.92 (2H, s), 8.90 (1H, s), 7.96 (2H, s), 7.44-7.41 (8H, m), 7.31-7.28 (4H, m), 7.22-7.18 (1H, m), 7.13-7.11 (2H, m), 7.00-6.97 (2H, m), 2.00 (3H, s).

$^{13}$C-NMR (126 MHz, DMSO-d$_6$): δ (ppm)=152.59 (NHCONH), 143.70, 139.66, 137.95, 136.65, 129.51, 128.98, 128.40, 126.90, 122.26, 118.59, 116.47, 116.36, 20.96 (CH$_3$).

VI, C$_{26}$H$_{23}$N$_5$O$_4$S, M=501.6, N-(3,4-bis(3-phenylureido)phenyl)benzenesulfonamide MS (ESI):m/z (%)=500.1 (100) [M–H]$^-$.

$^1$H-NMR (500 MHz, DMSO-d$_6$): δ (ppm)=10.24 (1H, s), 9.11 (1H, s), 8.96 (1H, s), 8.09 (1H, s), 7.89 (1H, s), 7.85-7.84 (2H, m), 7.65-7.55 (4H, m), 7.50-7.47 (4H, m), 7.36 (1H, d, J=8.6 Hz), 7.31-7.25 (4H, m), 7.00-6.94 (2H, m), 6.85 (1H, dd, J=8.4, 1.4 Hz).

$^{13}$C-NMR (126 MHz, DMSO-d$_6$): δ (ppm)=153.41 (NHCONH), 152.79 (NHCONH), 139.86, 139.73, 139.71, 134.15, 132.99, 132.82, 129.21, 128.83, 128.76, 126.75, 126.40, 125.54, 121.92, 121.76, 118.22, 118.14, 115.35, 114.87.

VII, C$_{27}$H$_{25}$N$_5$O$_4$S, M=515.6, N-(3,4-bis(3-phenylureido)phenyl)tosylamide MS (ESI):m/z (%)=514.1 (88) [M–H]$^-$.

$^1$H-NMR (500 MHz, DMSO-d$_6$): δ (ppm)=10.16 (1H, s), 9.11 (1H, s), 8.96 (1H, s), 8.09 (1H, s), 7.88 (1H, s), 7.73-7.72 (2H, m), 7.63 (1H, d, J=2.4 Hz), 7.50-7.46 (4H, m), 7.36-7.33 (3H, m), 7.31-7.25 (4H, m), 7.00-6.94 (2H, m), 6.84 (1H, dd, J=8.7, 2.5 Hz), 2.34 (3H, s).

$^{13}$C-NMR (126 MHz, DMSO-d$_6$): δ (ppm)=153.42 (NHCONH), 152.79 (NHCONH), 143.17, 139.87, 139.72, 136.86, 134.34, 133.00, 129.66, 128.83, 128.76, 126.81, 126.23, 125.57, 121.91, 121.75, 118.22, 118.13, 115.13, 114.64, 20.98 (CH$_3$).

VIII, C$_{26}$H$_{22}$ClN$_5$O$_4$S, M=536.0, N-(3,4-bis(3-phenylureido)phenyl)-4-chlorobenzene-sulfonamide MS (ESI):m/z (%)=534.1 (100) [M–H]$^-$.

$^1$H-NMR (500 MHz, DMSO-d$_6$): δ (ppm)=10.28 (1H, s), 9.10 (1H, s), 8.95 (1H, s), 8.09 (1H, s), 7.90 (1H, s), 7.84-7.82 (2H, m), 7.65-7.63 (2H, m), 7.62 (1H, d, J=2.5 Hz), 7.50-7.47 (4H, m), 7.39 (1H, d, J=8.7 Hz), 7.31-7.25 (4H, m), 6.99-6.94 (2H, m), 6.84 (1H, dd, J=8.7, 2.5 Hz).

$^{13}$C-NMR (126 MHz, DMSO-d$_6$): δ (ppm)=153.36 (NHCONH), 152.77 (NHCONH), 139.82, 139.68, 138.50, 137.76, 133.71, 132.95, 129.37, 128.78, 128.72, 128.67, 126.70, 125.48, 121.89, 121.75, 118.22, 118.15, 115.72, 115.23.

IX, C$_{27}$H$_{25}$N$_5$O$_5$S, M=531.6, N-(3,4-bis(3-phenylureido)phenyl)-4-methoxybenzene-sulfonamide MS (ESI): m/z (%)=530.1 (100) [M–H]$^-$ $^1$H-NMR (500 MHz, DMSO-d$_6$): δ (ppm)=10.08 (1H, s), 9.10 (1H, s), 8.96 (1H, s), 8.08 (1H, s), 7.88 (1H, s), 7.78-7.76 (2H, m), 7.62-7.62 (1H, m), 7.50-7.46 (4H, m), 7.35 (1H, d, J=8.6 Hz), 7.31-7.25 (4H, m), 7.08-7.07 (2H, m), 7.00-6.94 (2H, m), 6.85-6.83 (1H, m), 3.80 (3H, s).

$^{13}$C-NMR (126 MHz, DMSO-d$_6$): δ (ppm)=162.40, 153.42 (NHCONH), 152.79 (NHCONH), 139.87, 139.72, 134.44, 132.97, 131.35, 128.96, 128.82, 128.75, 126.19, 125.54, 121.90, 121.74, 118.21, 118.13, 115.14, 114.66, 114.35, 55.59 (OCH$_3$)

X, C$_{29}$H$_{29}$N$_5$O$_4$S, M=543.6, N-(3,4-bis(3-(4-tolyl)ureido)phenyl)tosylamide MS (ESI): m/z (%)=542.2 (38) [M–H]$^-$.

$^1$H-NMR (500 MHz, DMSO-d$_6$): δ (ppm)=10.13 (1H, s), 8.99 (1H, s), 8.84 (1H, s), 8.03 (1H, s), 7.82 (1H, s), 7.72-7.70 (2H, m), 7.61 (1H, d, J=2.2 Hz), 7.37-7.30 (7H, m), 7.11-7.06 (4H, m), 6.81 (1H, dd, J=8.7, 2.2 Hz), 2.34 (3H, s), 2.24 (3H, s), 2.23 (3H, s).

$^{13}$C-NMR (126 MHz, DMSO-d$_6$): δ (ppm)=153.43 (NHCONH), 152.80 (NHCONH), 143.14, 137.29, 137.13, 136.86, 134.19, 132.97, 130.72, 130.52, 129.64, 129.21, 129.15, 126.80, 126.27, 125.44, 118.31, 118.22, 115.05, 114.62, 20.97 (CH$_3$), 20.34 (CH$_3$), 20.33 (CH$_3$).

XI, C$_{29}$H$_{29}$N$_5$O$_6$S, M=575.6, bi-(3,4-bis(3-(4-methoxyphenyl)ureido)phenyl)tosylamide MS (ESI): m/z (%)=574.2 (80) [M–H]$^-$.

$^1$H-NMR (500 MHz, DMSO-d$_6$): δ (ppm)=10.12 (1H, s), 8.91 (1H, s), 8.76 (1H, s), 8.00 (1H, s), 7.79 (1H, s), 7.72-7.70 (2H, m), 7.60 (1H, d, J=2.5 Hz), 7.39-7.30 (7H, m), 6.90-6.84 (4H, m), 6.81 (1H, dd, J=8.7, 2.5 Hz), 3.71 (3H, s), 3.70 (3H, s), 2.34 (3H, s).

$^{13}$C-NMR (126 MHz, DMSO-d$_6$): δ (ppm)=154.52 (NHCONH), 154.40 (NHCONH), 153.59, 152.97, 143.14, 136.87, 134.15, 133.06, 132.91, 132.74, 129.64, 126.80, 126.40, 125.43, 120.03, 119.94, 115.02, 114.65, 114.03, 113.96, 55.16 (OCH$_3$), 55.13 (OCH$_3$), 20.97 (CH$_3$).

XII, C$_{39}$H$_{33}$N$_5$O$_6$S, M=699.8, N-(3,4-bis(3-(4-phenoxyphenyl)ureido)phenyl)tosylamide MS (ESI): m/z (%)=700.2 (100) [M+H]$^+$, 515.1 (63) [M+H–Ar$^2$NH$_2$]$^+$, 489.2 (43) [M+H–Ar$^2$NH$_2$–Ar$^2$NCO]$^+$.

$^1$H-NMR (500 MHz, DMSO-d0:6 (ppm)=10.14 (1H, s), 9.12 (1H, s), 8.98 (1H, s), 8.07 (1H, s), 7.87 (1H, s), 7.73-7.72 (2H, m), 7.62 (1H, d, J=2.4 Hz), 7.52-7.48 (4H, m), 7.38-7.33 (7H, m), 7.10-7.06 (2H, m), 7.01-6.94 (8H, m), 6.84 (1H, dd, J=8.7, 2.5 Hz), 2.34 (3H, s).

$^{13}$C-NMR (126 MHz, DMSO-d$_6$): δ (ppm)=157.61, 157.58, 153.47 (NHCONH), 152.86 (NHCONH), 150.77, 150.60, 143.09, 136.87, 135.84, 135.65, 134.32, 132.99, 129.85, 129.83, 129.59, 126.76, 126.30, 125.53, 122.75, 122.70, 119.94, 119.86, 119.69, 119.67, 117.65, 117.57, 115.16, 114.69, 20.93 (CH$_3$).

XIII, C$_{27}$H$_{23}$Cl$_2$N$_5$O$_4$S, M=584.5, N"-(3,4-bis(3-(4-chlorophenyl)ureido)phenyl)tosylamide MS (ESI): m/z (%)=582.1 (54) [M–H]$^-$.

$^1$H-NMR (500 MHz, DMSO-d$_6$): δ (ppm)=10.16 (1H, s), 9.24 (1H, s), 9.11 (1H, s), 8.10 (1H, s), 7.89 (1H, s), 7.72-7.70 (2H, m), 7.60 (1H, d, J=2.2 Hz), 7.51-7.48 (4H, m), 7.35-7.29 (7H, m), 6.83 (1H, dd, J=8.7, 2.3 Hz), 2.34 (3H, s).

$^{13}$C-NMR (126 MHz, DMSO-d$_6$): δ (ppm)=153.30 (NHCONH), 152.67 (NHCONH), 143.17, 138.86, 138.69, 136.82, 134.51, 132.93, 129.64, 128.65, 128.58, 126.79, 126.09, 125.74, 125.45, 125.27, 119.72, 119.64, 115.23, 114.62, 20.97 (CH$_3$).

XIV, C$_{31}$H$_{29}$N$_5$O$_6$S, M=599.7, N-(3,4-bis(3-(4-acetylphenyl)ureido)phenyl)tosylamide MS (ESI): m/z (%)=598.1 (82) [M–H]$^-$, 463.1 (23) [M–H–Ar$^2$NH$_2$]$^-$, 302.0 (11) [M–H–Ar$^2$NH$_2$–Ar$^2$NCO]$^-$.

$^1$H-NMR (500 MHz, DMSO-d$_6$): δ (ppm)=10.21 (1H, s), 9.53 (1H, s), 9.40 (1H, s), 8.22 (1H, s), 8.01 (1H, s), 7.93-7.91 (2H, m), 7.91-7.89 (2H, m), 7.73-7.71 (2H, m), 7.64 (1H, d, J=2.3 Hz), 7.62-7.58 (4H, m), 7.37-7.34 (3H, m), 6.86 (1H, dd, J=8.7, 2.3 Hz), 2.52 (3H, s), 2.50 (3H, s), 2.34 (3H, s).

$^{13}$C-NMR (126 MHz, DMSO-d$_6$): δ (ppm)=196.28, 196.26, 153.09 (NHCONH), 152.44 (NHCONH), 144.49, 144.31, 143.23, 136.80, 134.75, 132.88, 130.54, 130.39, 129.69, 129.69, 129.65, 126.82, 125.94, 125.89, 117.19, 117.11, 115.35, 114.60, 26.33 (CH$_3$), 26.31 (CH$_3$), 20.99 (CH$_3$).

XV, C$_{29}$H$_{23}$F$_6$N$_5$O$_4$S, M=651.6, N-(3,4-bis(3-(2-(trifluoromethyl)phenyl)ureido)phenyl)tosylamide MS (HSI): m/z (%)=650.1 (100) [M–H]$^-$, 489.1 (20) [M–H–Ar$^2$NH$_2$]$^-$, 302.1 (16) [M–H–Ar$^2$NH$_2$–Ar$^2$NCO]$^-$.

$^1$H-NMR (500 MHz, DMSO-d$_6$): δ (ppm)=10.15 (1H, s), 8.77 (1H, s), 8.66 (1H, s), 8.46 (1H, s), 8.26 (1H, s), 7.98-7.92 (2H, m), 7.71-7.57 (7H, m), 7.37-7.33 (3H, m), 7.30-7.27 (1H, m), 7.25-7.22 (1H, m), 6.85 (1H, dd, J=8.7, 2.3 Hz), 2.33 (3H, s).

$^{13}$C-NMR (126 MHz, DMSO-d$_6$): δ (ppm)=153.39 (NHCONH), 153.00 (NHCONH), 143.17, 136.80, 136.59, 136.35, 134.41, 132.81, 132.54, 129.62, 126.77, 126.28, 126.09, 125.92, 125.40, 125.07, 123.88, 123.49, 122.90, 120.31, 119.65, 115.30, 20.93 (CH$_3$).

XVI, C$_{29}$H$_{25}$N$_5$O$_6$S, M=571.6, N,N'-(((4-tosylamido-1,2-phenylene)bis(azandiyl))bis(carbonyl))dibenzamide MS (ESI): m/z (%)=570.1 (25) [M–H]$^-$, 449.0 (100) [M–H–Ar$^2$NH$_2$]$^-$, 302.0 (63) [M–H–Ar$^2$NH$_2$–Ar$^2$NCO]$^-$.

$^1$H-NMR (500 MHz, DMSO-d$_6$): δ (ppm)=11.09 (1H, s), 11.08 (1H, s), 10.85 (1H, s), 10.45 (1H, s), 10.37 (1H, s), 8.01-7.99 (2H, m), 7.96-7.94 (2H, m), 7.83 (1H, d, J=2.5 Hz), 7.77-7.75 (2H, m), 7.65-7.60 (2H, m), 7.53-7.46 (5H, m), 7.37-7.36 (2H, m), 6.97 (1H, dd, J=8.7, 2.5 Hz), 2.34 (3H, s).

$^{13}$C-NMR (126 MHz, DMSO-d$_6$): δ (ppm)=168.70, 168.64, 152.23 (NHCONH), 151.43 (NHCONH), 143.30, 136.79, 135.88, 132.97, 132.90, 132.57, 132.39, 132.21, 129.69, 128.47, 128.47, 128.24, 128.23, 126.81, 126.44, 124.87, 115.83, 114.38, 20.96 (CH$_3$).

XVII, C$_{26}$H$_{23}$N$_5$O$_4$S, M=501.6, N-phenyl-2,4-bis(3-phenylureido)benzenesulfonamide MS (ESI): m/z (%)=500.1 (100) [M–H]$^-$, 381.1 (22) [M–H–Ar$^2$NCO]$^-$.

$^1$H-NMR (500 MHz, DMSO-d$_6$): δ (ppm)=10.28 (1H, s), 9.65 (1H, s), 9.15 (1H, s), 8.67 (1H, s), 8.48 (1H, s), 8.15 (1H, d, J=1.2 Hz), 7.67 (1H, d, J=8.8 Hz), 7.56-7.54 (2H, m), 7.47-7.46 (2H, m), 7.37-7.27 (5H, m), 7.24-7.21 (2H, m), 7.13-7.12 (2H, m), 7.03-6.98 (3H, m).

$^{13}$C-NMR (126 MHz, DMSO-d$_6$): δ (ppm)=152.04 (NHCONH), 151.75 (NHCONH), 144.48, 139.68, 139.18, 138.16, 137.24, 130.32, 129.13, 128.81, 128.77, 124.34, 122.28, 122.16, 120.67, 119.07, 118.54, 118.47, 111.07, 110.68.

XVIII, C$_{29}$H$_{27}$N$_5$O$_6$S, M=573.6, ethyl 4-(2,4-bis(3-phenylureido)phenylsulfonamido)benzoate MS (ESI):m/z (%)=572.1 (100) [M–H]$^-$.

$^1$H-NMR (500 MHz, DMSO-d$_6$): δ (ppm)=10.77 (1H, s), 9.60 (1H, s), 9.15 (1H, s), 8.66 (1H, s), 8.38 (1H, s), 8.07 (1H, d, J=2.1 Hz), 7.81-7.80 (2H, m), 7.74 (1H, d, J=8.9 Hz), 7.50-7.48 (2H, m), 7.45-7.43 (2H, m), 7.37 (1H, dd, J=8.9, 2.1 Hz), 7.32-7.26 (4H, m), 7.24-7.22 (2H, m), 7.02-6.97 (2H, m), 4.19 (2H, q, J=7.1 Hz), 1.24 (3H, t, J=7.1 Hz).

$^{13}$C-NMR (126 MHz, DMSO-d$_6$): δ (ppm)=165.02, 151.95 (NHCONH), 151.59 (NHCONH), 144.72, 141.88, 139.54, 139.11, 138.09, 130.46, 130.33, 128.77, 128.70, 124.94, 122.26, 122.10, 118.99, 118.82, 118.43, 118.43, 111.23, 111.01, 60.41 (CH$_3$), 14.08 (CH$_3$).

XIX, C$_{32}$H$_{28}$N$_6$O$_6$S$_2$, M=656.7, N$^1$,N$^3$-diphenyl-4,6-bis(3-phenylureido)benzene-1,3-disulfonamide MS (ESI): m/z (%)=655.1 (100) [M–H]$^-$, 536.1 (18) [M–H–Ar$^2$NCO]$^-$.

$^1$H-NMR (500 MHz, DMSO-d$_6$): δ (ppm)=10.47 (2H, s), 9.75 (2H, s), 8.85 (1H, s), 8.52 (2H, s), 8.15 (1H, s), 7.48-7.47 (4H, m), 7.32-7.29 (4H, m), 7.21-7.18 (4H, m), 7.04-7.02 (8H, m).

$^{13}$C-NMR (126 MHz, DMSO-d$_6$): δ (ppm)=150.92 (NHCONH), 141.38, 139.07, 136.38, 131.09, 129.19, 128.70, 124.80, 122.50, 121.03, 118.82, 118.75, 113.36.

An aqueous application suspension for forming the heat-sensitive colour-forming layer of a heat-sensitive recording paper was applied on a laboratory scale by means of a doctor bar to one side of a synthetic base paper (Yupo® FP680) with a grammage of 63 g/m$^2$. Once dry, a thermal recording material sheet was obtained. The applied amount of the heat-sensitive colour-forming layer was between 3.8 and 4.2 g/m$^2$.

A heat-sensitive recording material or thermal paper was produced on the basis of the details provided above, wherein the following formulation of aqueous application suspension was used to form a composite structure on a carrier substrate, and then the further layers, especially a protective layer, were formed in the usual manner, which will not be detailed separately here.

Preparation of the dispersions (in each case for 1 part by weight) for the application suspensions An aqueous dispersion A (colour former dispersion) was prepared by grinding 20 parts by weight of 3-N-n-dibutylamino-6-methyl-7-anilinofluorane (ODB-2) with 33 parts by weight of a 15% aqueous solution of Ghosenex™ L-3266 (sulfonated polyvinyl alcohol, Nippon Ghosei) in a bead mill.

An aqueous dispersion B (colour developer dispersion) was prepared by grinding 40 parts by weight of the colour developer together with 66 parts by weight of a 15% aqueous solution of Ghosenex™ L-3266 in the bead mill.

An aqueous dispersion C (sensitisation agent dispersion) was prepared by grinding 40 parts by weight of sensitisation agent with 33 parts by weight of a 15% aqueous solution of Ghosenex™ L-3266 in a bead mill.

All dispersions produced by grinding had a mean particle size D$_{(4,3)}$ of from 0.80 to 1.20 μm. The particle size distribution of the dispersions was measured by laser diffraction using a Coulter LS230 apparatus from Beckman Coulter.

The dispersion D (slip additive dispersion) was a 20% zinc stearate dispersion consisting of 9 parts by weight of Zn stearate, 1 part by weight of Ghosenex™ L-3266, and 40 parts by weight of water.

Pigment P was a 72% coating kaolin suspension (Lustra® S, BASF).

The binder consisted of a 10% aqueous polyvinyl alcohol solution (Mowiol 28-99, Kuraray Europe).

The heat-sensitive application suspension was prepared by mixing, under stirring, of 1 part A, 1 part B, 1 part C, 56 parts D, 146 parts pigment P, and 138 parts binder solution (all parts by weight) under consideration of the order of introduction B, D, C, P, A binder, and by bringing the mixture with water to a solid content of approximately 25%.

The heat-sensitive coating suspensions thus obtained were used to produce composite structures of paper carrier and thermal reaction layer.

The thermal recording materials were assessed as described hereinafter (Tables 3, 4 and 5).

(1) Dynamic Colour Density:

The papers (strips 6 cm wide) were thermally printed with use of an Atlantek 200 test printer (Atlantek, USA) with a Kyocera printhead of 200 dpi and 560 ohms with an applied voltage of 20.6 V and a maximum pulse width of 0.8 ms with a chequered pattern with 10 energy gradations. The image density (optical density (o.d.)) was measured using a Macbeth densitometer RD-914 from Gretag at an energy stage of 0.45 mJ/dot. The measurement uncertainty of the o.d. values was estimated at ≥2%.

(2) Static Colour Density (Starting Temperature):

The recording material sheet was pressed against a series of thermostatically controlled metal dies heated to different temperatures with a press-on pressure of 0.2 kg/cm$^2$ and a contact time of 5 sec. (thermal tester TP 3000QM, Maschinenfabrik Hans Rychiger AG, Steffisburg, Switzerland). The image density (optical density) of the images thus produced was measured using a Macbeth densitometer RD-914 from Gretag. The static starting point, according to definition, is the lowest temperature at which an optical density of 0.2 is achieved. The accuracy of the measurement method was ≥±0.5° C.

(3) Resistance Test of the Printed Image:

a) Resistance of the printed image under conditions of artificial ageing:

Each sample of the thermal recording paper recorded dynamically in accordance with the method under (1) was stored for 7 days under the following conditions:

i) 50° C. (dry ageing),
ii) 40° C., 85% relative humidity (moist ageing) and
iii) under artificial light of fluorescent tubes, illuminance 16000 Lux (light ageing)

Once the test period had elapsed, the image density was measured at an energisation energy of 0.45 mJ/dot and was set in relation to the corresponding image density values before the artificial ageing in accordance with the formula (Eq. 1).

b) plasticiser resistance:

A plasticiser-containing cling film (PVC film with 20-25% dioctyl adipate) was brought into contact with the sample of the thermal recording paper, which had been dynamically recorded in accordance with the method under (1), avoiding folds and inclusions of air, then rolled up into a roll and stored for 16 hours. One sample was stored at room temperature (20-22° C.), and a second sample was stored at 40° C. After removal of the film, the image density (o.d.) was measured and set in relation to the corresponding image density values before the action of the plasticiser in accordance with formula (Eq. 1).

c) resistance to adhesive:

A strip of transparent self-adhesive tape from Tesa (tesafilm® crystal-clear, #57315), and separately therefrom a strip of packaging adhesive tape from Tesa (#04204) were adhered to the sample of the thermal recording paper, which had been dynamically recorded in accordance with the method under (1), avoiding folds and inclusions of air. After storage at room temperature (20-22° C.), the image density (o.d.) was measured after 24 hours and after 7 days-through the particular adhesive tape—and, in accordance with the formula (Eq. 1), was set in relation to the similarly determined image density values of a freshly adhered specimen.

$$\% \text{ remaining image density} = \frac{\text{image density after test}}{\text{image density before test}} * 100 \quad \text{(Eq. 1)}$$

The scattering of the % values calculated by (Eq. 1) was ≤±2 percentage points.

4) Storage Suitability of the Unprinted Thermal Paper:

A sheet of recording paper was cut into three identical strips. One strip was recorded dynamically in accordance with the method under (1) and the image density was determined. The two other strips were stored in the unprinted (white) state for 4 weeks in a climate of a) 40° C. and 85% relative humidity (r.h.) and b) 60° C. and 50% relative humidity (r.h.).

After climatisation of the papers at room temperature, they were dynamically printed in accordance with the method under (1) and the image density with an energisation energy of 0.45 mJ/dot was determined using the densitometer. The remaining writing performance (%) of the stored specimens in relation to the fresh (un-aged) specimens was calculated in accordance with the following equation (Eq. 1).

Tables 3 to 5 summarise the evaluation of the finished recording materials.

TABLE 3

Image density, starting temperature and artificial ageing

| Colour developer | o.d. (0.45 mJ/dot) | Starting point (° C.) | Artificial ageing* | | |
|---|---|---|---|---|---|
| | | | dry | moist | light |
| III | 1.19 | 79 | 97 | 98 | 86 |
| IV | 1.17 | 82 | 96 | 98 | 80 |
| XIV | 1.18 | 85 | 100 | 98 | 87 |
| XVII | 1.19 | 82 | 97 | 100 | 74 |
| XVIII | 1.22 | 81 | 98 | 100 | 76 |
| XIX | 1.29 | 80 | 98 | 99 | 80 |
| Y | 1.23 | 82 | 100 | 98 | 72 |
| Z | 1.25 | 84 | 99 | 98 | 80 |
| PF201 | 1.23 | 76 | 100 | 96 | 82 |

*Percentage of remaining image density in accordance with Eq. 1

TABLE 4

Resistance of the printed image

| Colour developer | Tesa adhesive tape* | | | | Plasticiser film* | |
|---|---|---|---|---|---|---|
| | 24 h | | 7 days | | 16 h | |
| | #57315 | #04204 | #57315 | #04204 | R.T. | 40° C. |
| III | 85 | 80 | 65 | 38 | 96 | 75 |
| IV | 92 | 89 | 73 | 60 | 95 | 71 |
| XIV | 90 | 95 | 75 | 79 | 99 | 91 |
| XVII | 78 | 54 | 50 | 14 | 96 | 78 |
| XVIII | 80 | 66 | 51 | 30 | 97 | 80 |
| XIX | 81 | 61 | 58 | 21 | 99 | 80 |
| Y | 32 | 11 | 9 | 7 | 67 | 7 |
| Z | 54 | 31 | 13 | 16 | 88 | 32 |
| PF201 | 71 | 43 | 29 | 11 | 96 | 68 |

*Percentage of remaining image density in accordance with Eq. 1

TABLE 5

Writing performance after storage

| Colour developer | o.d. before storage | 4 weeks 40° C./85% r.h. | | 4 weeks 60° C./50% r.h. | |
|---|---|---|---|---|---|
| | | o.d. after storage | remaining o.d. (%) | o.d. after storage | remaining o.d. (%) |
| III | 1.19 | 1.18 | 99 | 1.05 | 88 |
| IV | 1.17 | 1.12 | 96 | 1.05 | 90 |
| XIV | 1.18 | 1.16 | 98 | 1.01 | 86 |
| XVII | 1.19 | 1.18 | 99 | 1.02 | 86 |
| XVIII | 1.22 | 1.16 | 95 | 1.04 | 85 |
| XIX | 1.29 | 1.29 | 100 | 1.11 | 86 |
| Y | 1.23 | — | — | 1.05 | 85 |
| Z | 1.25 | 1.25 | 100 | 1.11 | 89 |
| PF201 | 1.23 | 1.19 | 97 | 0.74 | 60 |

It can be seen from the examples above that the heat-sensitive recording material of the present invention presents the following advantageous properties especially:

(1) The recorded image of the heat-sensitive papers with the colour developers according to the invention has a print density (optical density) which is comparable to that of the developers of the comparison specimens (Table 3).

(2) The temperature from which a visually noticeable greying of the papers according to the invention occurred (static starting point) is comparable to or higher than that for the comparison papers and satisfies the requirements of marketable heat-sensitive recording materials (Table 3).

(3) The papers subjected to the ageing test demonstrate a high image resistance. This is better than or comparable to that of the comparison papers (Table 3).

(4) The printed image is practically not faded following the action hydrophobic agents (adhesives, plasticisers). The image resistance is better or comparable to the performance of the known non-phenolic colour developers (Table 4).

(5) The printing of the recording materials stored over several weeks under extreme conditions leads to image densities which are practically identical to those of unstored (fresh) paper (Table 5).

(6) A heat-sensitive recording material of high quality in respect of all key application properties can be obtained with the colour developers according to the invention. No heat-sensitive recording material obtained using colour developers according to the prior art has a comparable balanced performance profile across all properties.

(7) The comparison of the heat-sensitive recording material containing the colour developer Y with heat-sensitive recording materials containing the colour developers XVII and XIX, and of the heat-sensitive recording material containing the colour developer Z with heat-sensitive recording materials containing the colour developers III and IV reveals the increase in image resistance, which, with otherwise comparable chemistry, is due to the increase in the density of the functional groups involved in the colour-forming and stabilisation process (Table 4).

The invention claimed is:
1. A compound of formula (I),
$Ar(NHSO_2A^1)_l(SO_2NHAr^1)_m(NHC(O)NHAr^2)_n$ (I),
wherein
l and m independently of one another are 0, 1, 2, 3 and/or 4 and the sum of l+m is equal to or greater than 1,
n is 2, 3, 4 or 5,
Ar is a benzene ring substituted (l+m+n) times,
$Ar^1$ is an unsubstituted or substituted aromatic group, and

Ar² is an unsubstituted or substituted phenyl group or an unsubstituted or substituted benzoyl group.

2. The compound according to claim 1, wherein l is 0 or 1.

3. The compound according to claim 1, wherein m is 0, 1 or 2.

4. The compound according to claim 1, wherein n is 2.

5. The compound according to claim 1, wherein l is 1, m is 0, and n is 2.

6. The compound according to claim 1, wherein l is 0, m 1, and n is 2.

7. The compound according to claim 1, wherein l is 0, m is 2, and n is 2.

8. The compound according to claim 1, wherein Ar is a benzene ring substituted 3 or 4 times.

9. The compound according to claim 1 wherein Ar¹ is an unsubstituted or substituted phenyl group.

10. The compound according to claim 1, wherein Ar¹ is a monosubstituted phenyl group substituted with a $C_1$-$C_5$ alkyl, an alkenyl, an alkynyl, a benzyl, an RO, a halogen, formyl, an ROC, an $RO_2C$, a CN, $NO_2$, an R—$SO_2O$, are RO—$SO_2$, R—NH—$S_{02}$, an R—$SO_2$—NH, an R—NH—CO—NH, an R—$SO_2$—NH—CO—NH, n R—NH—CO—NH—R or an R—CO—NH group, wherein R is a $C_1$-$C_5$ alkyl, an alkenyl, an alkynyl, a phenyl, a tolyl or a benzyl group.

11. The compound according to claim 10, wherein the monosubstituted phenyl group is substituted with a 4-$C_1C_5$ alkyl, a 4-RO or a 4-($RO_2C$) group, wherein R is a $C_1$ to $C_5$ alkyl group.

12. The compound according to claim 10, wherein Ar² is a substituted phenyl group which is substituted with $C_1$-$C_4$ alkyl, a halogen, a $CX_3$, formyl, an ROC, an $RO_2C$, a CN, an $NO_2$ or an RO group, wherein X is a halogen group and A is a $C_1$-$C_5$ alkyl group, a phenyl group or a tolyl group.

13. A heat-sensitive recording material comprising a carrier substrate, at least one colour former, and at least one heat-sensitive colour-forming layer containing at least one phenol-free colour developer, wherein the at least one phenol-free colour developer is a compound of formula (I) according to claim 1 which contains no phenol substituents.

14. The heat-sensitive recording material according to claim 13, wherein the at least one colour former is a dye of the triphenylmethane type, of the fluorane type, of the azaphthalide type and/or of the fluorene type.

15. The heat-sensitive recording material according to claim 13, wherein, besides the compound of formula (I), one or more further non-phenolic colour developer(s) is/are present.

16. The heat-sensitive recording material according to claim 13, wherein the compound of formula (I) is present in an amount of from approximately 3 to approximately 35% by weight, in relation to the total solid content of the heat-sensitive layer.

17. The compound according to claim 1, wherein Ar is a benzene ring substituted 3 times.

18. The compound according to claim 1, wherein Ar¹ is a monosubstituted phenyl group.

19. The heat-sensitive recording material according to claim 13, wherein the compound of formula (I) is present in an amount of from approximately 10 to 25% by weight, in relation to the total solid content of the heat-sensitive layer.

20. The compound according to claim 1, wherein Ar¹ is a 4-alkylester phenyl group.

* * * * *